US009952299B2

(12) United States Patent
Greiser (10) Patent No.: US 9,952,299 B2
(45) Date of Patent: Apr. 24, 2018

(54) METHOD AND APPARATUS TO DETERMINE A MAGNETIC RESONANCE RELAXATION TIME IN THE HEART MUSCLE IN A MAGNETIC RESONANCE EXAMINATION

(75) Inventor: Andreas Greiser, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 774 days.

(21) Appl. No.: 12/780,072

(22) Filed: May 14, 2010

(65) Prior Publication Data

US 2010/0292561 A1    Nov. 18, 2010

(30) Foreign Application Priority Data

May 15, 2009    (DE) .................... 10 2009 021 492

(51) Int. Cl.

| | |
|---|---|
| A61B 5/05 | (2006.01) |
| G01R 33/50 | (2006.01) |
| A61B 5/055 | (2006.01) |
| G01R 33/24 | (2006.01) |
| G01R 33/56 | (2006.01) |
| G01R 33/561 | (2006.01) |

(52) U.S. Cl.
CPC ............ G01R 33/50 (2013.01); A61B 5/055 (2013.01); G01R 33/24 (2013.01); G01R 33/5602 (2013.01); G01R 33/5608 (2013.01); G01R 33/5616 (2013.01); G01R 33/5617 (2013.01)

(58) Field of Classification Search
USPC ....... 600/407, 410, 450, 456, 458, 475, 479, 600/508, 509, 524; 324/306, 307, 309, 324/312, 317, 319
See application file for complete search history.

(56) References Cited

U.S. PATENT DOCUMENTS

| | | | | |
|---|---|---|---|---|
| 4,694,252 A | * | 9/1987 | Riederer et al. | 324/309 |
| 5,908,386 A | * | 6/1999 | Ugurbil et al. | 600/410 |
| 6,271,665 B1 | * | 8/2001 | Berr | G01R 33/56341 324/306 |

(Continued)

OTHER PUBLICATIONS

Ballester et al., "Estimation of the Partial Volume Effect in MRI", Medical Image Analysis 6 (2002), pp. 389-405.*

(Continued)

Primary Examiner — James Kish
(74) Attorney, Agent, or Firm — Schiff Hardin LLP (57) ABSTRACT

In a method and magnetic resonance (MR) system to determine an MR relaxation time (for example a T1, T2 or T2* relaxation time) in the heart muscle in a magnetic resonance examination, a determination an annular slice image region of the heart muscle of the left heart chamber in MR image data with the use of an automatic image segmentation. Multiple sub-regions within the slice image region are automatically determined. Each sub-region respectively includes multiple pixels of the annular slice image region of the heart muscle of the left heart chamber. An MR relaxation time is determined automatically for each of the multiple sub-regions and associated with the corresponding sub-region. A characteristic MR relaxation time in the heart muscle is determined by a statistical analysis of the multiple MR relaxation times that are associated with the multiple sub-regions.

10 Claims, 5 Drawing Sheets

(56) References Cited

U.S. PATENT DOCUMENTS

| | | | | |
|---|---|---|---|---|
| 6,438,408 | B1* | 8/2002 | Mulligan et al. | 600/510 |
| 6,892,089 | B1* | 5/2005 | Prince et al. | 600/410 |
| 7,069,068 | B1* | 6/2006 | Ostergaard | 600/420 |
| 2002/0016543 | A1* | 2/2002 | Tyler | G06T 7/0012 600/410 |
| 2003/0142857 | A1* | 7/2003 | Alyassin | G06T 5/20 382/131 |
| 2004/0102692 | A1* | 5/2004 | Schenck | A61B 5/055 600/410 |
| 2005/0203395 | A1* | 9/2005 | Sui | A61B 8/08 600/437 |
| 2005/0232506 | A1* | 10/2005 | Smith et al. | 382/254 |
| 2005/0256393 | A1* | 11/2005 | Deoni | G01R 33/50 600/410 |
| 2007/0106150 | A1* | 5/2007 | Greiser et al. | 600/413 |
| 2008/0108894 | A1* | 5/2008 | Elgavish | G06T 7/0012 600/420 |
| 2008/0242973 | A1* | 10/2008 | Warmuth | 600/413 |
| 2008/0292169 | A1* | 11/2008 | Wang et al. | 382/131 |
| 2008/0312527 | A1* | 12/2008 | Masumoto et al. | 600/425 |
| 2010/0111380 | A1* | 5/2010 | Kawagishi | G06T 7/0012 382/128 |

OTHER PUBLICATIONS

Sparrow et al., "Myocardial T1 Mapping for Detection of Left Ventricular Myocardial Fibrosis in Chronic Aortic Regurgitation: Pilot Study." American Journal of Roentgenology, Dec. 2006, vol. 187, No. 6, pp. 1-13. Proper citation: American Journal of Roentgenology. 2006;187: W630W635. 10.2214/AJR.05.1264.*

Cerqueira et al., "Standardized Myocardial Segmentation and Nomenclature for Tomographic Imaging of the Heart." Circulation; Jan. 29, 2002; 105. pages 539-542.*

Bazelaire, et al., "MR Imaging Relaxation Times of Abdominal and Pelvic Tissues Measured in Vivo at 3.0 T: Preliminary Results." Radiology 2004; 230. pp. 652-659.*

Giri et al., "T2 quantification for improved detection of myocardial edema". J Cardiovasc Magn Reson. 2009; 11(1): 56. pp. 1-13.*

"Myocardial $T*_2$ Measurements in Iron-Overloaded Thalassemia: An In Vivo Study to Investigate Optimal Methods of Quantification," He et al., Magnetic Resonance in Medicine, vol. 60 (2008) pp. 1082-1089.

"Myocardial $T*_2$ Measurements in Iron-Overloaded Thalassemia: An Ex Vivo Study to Investigate Optimal Methods of Quantification," He et al., Magnetic Resonance in Medicine, vol. 60 (2008) pp. 350-356.

"Left Ventricular Diastolic Function Compared With T2* Cardiovascular Magnetic Resonance for Early Detection of Myocardial Iron Overload in Thalassemia Major," Westwood et al., Journal of Magnetic Resonance Imaging, vol. 22 (2005) pp. 229-233.

"Interscanner Reproducibility of Cardiovascular Magnetic Resonance T2* Measurements of Tissue Iron in Thalassemia," Westwood et al., Journal of Magnetic Resonance Imaging, vol. 18 (2003) pp. 616-620.

"A Single Breath-Hold Multiecho T2* Cardiovascular Magnetic Resonance Technique for Diagnosis of Myocardial Iron Overload," Westwood et al., Journal of Magnetic Resonance Imaging, vol. 18 (2003) pp. 33-39.

"Cardiovascular T2-star (T2*) Magnetic Resonance for the Early Diagnosis of Myocardial Iron Overload" Anderson et al., European Heart Journal, vol. 22 (2001) pp. 2171-2179.

* cited by examiner

METHOD AND APPARATUS TO DETERMINE A MAGNETIC RESONANCE RELAXATION TIME IN THE HEART MUSCLE IN A MAGNETIC RESONANCE EXAMINATION

BACKGROUND OF THE INVENTION

Field of the Invention

The present invention concerns a method to determine a magnetic resonance (MR) relaxation time, in particular a T2* relaxation time, in the heart muscle in a magnetic resonance examination.

Description of the Prior Art

A determination of the MR relaxation times—for example a relaxation time T2*, a T1 relaxation time or a T2 relaxation time—is helpful in a number of magnetic resonance examinations.

For example, a determination of the transversal relaxation time T2* is appropriate in magnetic resonance measurements (MR) for a diagnosis of thalassemia. Thalassemia is a genetically caused abnormality in hemoglobin production. Left untreated, patients can possibly suffer from anemia that is accompanied by an increased iron concentration in the heart muscle (myocardium). Evidence of the iron concentration in the myocardium is primarily relevant for therapy. A change in the iron concentration results in a shortening of the T2* time in a magnetic resonance measurement. Exact quantitative information about the T2* time is therefore desirable.

According to the prior art, a quantification of the T2* relaxation time in the myocardium can be achieved using a multi-gradient echo measurement with suitably selected echo times TE1 ... TEn. At first, however, only individual images (frames) with varying contrast result from this measurement, from which the T2* time is still not quantitatively apparent. Therefore the images of the multi-gradient echo measurement are evaluated with an interactive auxiliary program (for example CMRtools). The goal of the additional evaluation is to establish a region of interest (ROI) of an optimally standardized (reference) tissue region in the left ventricle. A region from the ventricular septum is typically selected as a standardized tissue region. The signal intensity of this tissue region is then approximated as a function of the echo time to an exponential fit, i.e. with the use of an adapted exponential function. The T2* time for this tissue region results from the multiple images of the multi-gradient echo measurement.

This interactive evaluation of the images of the multi-gradient echo measurement requires additional auxiliary programs as well as an interaction of the user or treating physician, and is therefore time-consuming, costly and/or even error prone given an operating error.

According to the prior art, a quantitative determination of additional MR relaxation times in the heart muscle—for example a determination of T1 or T2 relaxation time—is likewise complicated.

SUMMARY OF THE INVENTION

An object of the present invention is to provide an improved method to determine an MR relaxation time in the heart muscle.

According to the present invention, this object is achieved by a method to determine an MR relaxation time in the heart muscle, a magnetic resonance system to determine an MR relaxation time in the heart muscle, and an electronically readable data storage medium.

According to the invention, a method is provided to determine an MR relaxation time in the heart muscle in a magnetic resonance examination. The MR relaxation time can be, for example, the T1 relaxation time, the T2 relaxation time or the T2* relaxation time. The method operates on MR image data. The MR image data can represent multiple images. In the case of determination of T1 relaxation time, the multiple images can be acquired with the use of an inversion recovery sequence with different inversion times. In the case of determination of T2 relaxation time, multiple images can be acquired with the use of a spin echo sequence with different echo times. In the case of determination of T2* relaxation time, multiple images of a multi-gradient echo measurement can be acquired with different echo times. An annular slice image region of the heart muscle of the left heart chamber (i.e. of the left ventricle) is determined in the MR image data with the use of an automatic image segmentation. Multiple sub-regions are determined automatically within the annular slice image region, meaning that the slice image region is automatically subdivided into multiple sub-regions. Each sub-region includes multiple pixels of the annular slice image region of the heart muscle of the left heart chamber. The multiple sub-regions can each include, for example, an annular segment of the annular slice image region. An MR relaxation time is determined automatically for each of the multiple sub-regions. A characteristic MR relaxation time that is valid for the entire heart muscle is then determined automatically using a statistical analysis of the multiple MR relaxation times associated with the different sub-regions.

The determination of the annular slice image region of the heart muscle of the left heart chamber is already possible without user interaction with a technique known as "inline segmentation" that is available according to the prior art. A region that is suitable for the relaxation time quantification can be determined automatically based on the epicardial and subendocardial boundary lines that are acquired in this manner that border the annular slice image region. However, the inline segmentation algorithm known according to the prior art cannot automatically detect the septal region, which would be suitable as a reference tissue region to determine the T2* time, for example. Therefore, according to the method of the present invention the annular slice image region is divided into multiple sub-regions and a corresponding relaxation time is determined for each sub-region. A statistical analysis of these multiple relaxation times that are respectively associated with the multiple sub-regions then delivers the characteristic value of the relaxation time. The method according to the invention is thus suitable to determine an MR relaxation time in the heart muscle without a user interaction being necessary.

According to one embodiment, the multi-gradient echo measurement or the spin echo sequence is implemented with echo times in a range from 2 ms to 20 ms.

According to a further embodiment of the method, the width of the annular slice image region is reduced in the radial direction in that the inner circumference of the slice region is enlarged by a predetermined value and the outer circumference of the slice region is reduced by a predetermined value. The predetermined value can be a value in the range from 1-10 mm, for example, or can be a predetermined percentile of 5%-30% of the entire width of the annular region, for example. Partial volume effects in the border region of the ventricle can be avoided by this narrowing of the annular slice image region, so the reliability of the method is improved.

The automatic determination of the MR relaxation time by means of statistical analysis of the multiple MR relaxation times can be implemented, for example, by determining an average value of a predetermined portion of the multiple MR relaxation times is determined, and this average is additionally used as the characteristic MR relaxation time. The predetermined portion of the multiple MR relaxation times can include, for example, the largest of the MR relaxation times. The predetermined portion of the multiple MR relaxation times can be, for example, half of the multiple MR relaxation times. For example, if a T2* relaxation time is to be determined, the maximum T2* relaxation time of the multiple T2* relaxation times can alternatively be determined as a characteristic T2* relaxation time, because susceptibility effects in the region of the free wall of the left ventricle can lead to the signal decaying faster and the local T2* relaxation times thus being below the typically considered T2* relaxation time from the septal region.

Furthermore, according to the present invention, a magnetic resonance system is provided to determine an MR relaxation time in the heart muscle in a magnetic resonance examination. The magnetic resonance system has a control unit to control a scanner (data acquisition unit); a reception device to receive signals that are acquired by the scanner, and an evaluation device that evaluates the signals and generates MR image data. The evaluation device is designed to determine an annular slice image region of the heart muscle of the left heart chamber in the MR image data with the use of an automatic image segmentation. Within the annular slice image region, the evaluation device automatically determines multiple sub-regions and determines a respective MR relaxation time for each of the multiple sub-regions. The MR relaxation time in the heart muscle is then determined by the evaluation device by a statistical analysis of these multiple MR relaxation times that are associated with the multiple sub-regions. The magnetic resonance system is designed for implementation of the method described above.

The present invention also encompasses an electronically readable data storage medium—for example a control device or DVD—on which are stored (encoded) electronically readable control information, in particular software. All inventive embodiments of the method described in the preceding can be implemented with the magnetic resonance system when this control information is read from the data medium and stored in a control evaluation device of the magnetic resonance system.

DESCRIPTION OF THE PREFERRED EMBODIMENTS

Figure 7:
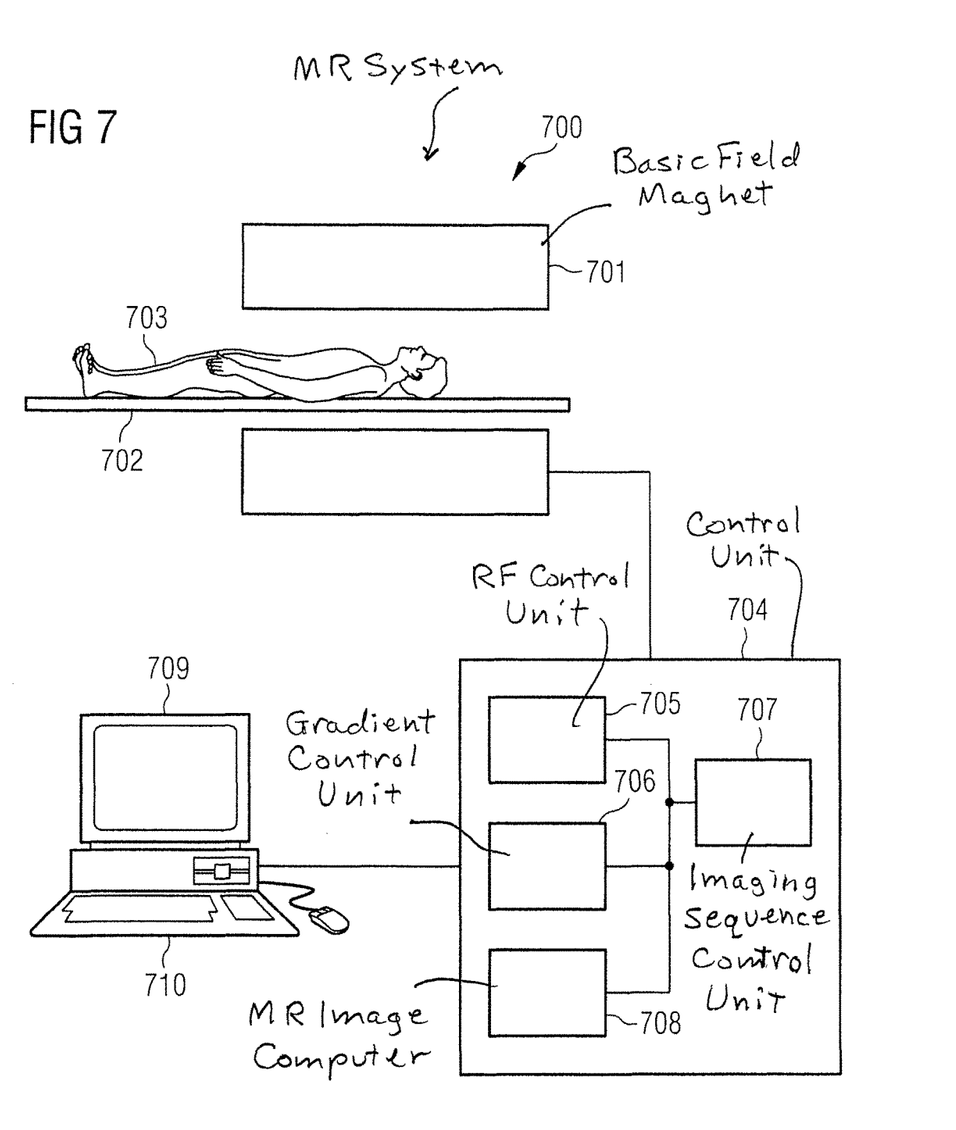
FIG. 7 schematically shows an MR system to determine an MR relaxation time in the heart muscle.

An MR system 700 with which an MR relaxation time in the heart muscle can be determined according to the invention in a magnetic resonance examination is shown in FIG. 7. The MR system 700 has a basic field magnet 701 that generates a polarization field B0. An examination person 703 arranged on a bed 702 is driven into the center of the basic field magnet 701 where the acquisition of the MR signals from an examination region is implemented via radiation of RF pulses and switching of gradients. How MR images—in particular images of a multi-gradient echo measurement—can be generated in a pulse sequence with a series of RF pulses and switching of gradients is known to those skilled in the art and need not be described in detail herein. The MR system 700 is connected with a central control unit 704 with which the MR system 700 is controlled. Among other things, the central control unit 704 has an RF control unit 705 which controls the switching of the RF pulses to deflect the magnetization. A gradient control unit 706 controls the switching of the gradient magnetic fields for spatial coding of the excited spins. An imaging sequence control unit 707 controls the workflow of the gradient switching, the RF pulses and the signal readout depending on the selected imaging sequence. An MR image computer 708 calculates MR images in a known manner via Fourier transformation from the MR signals detected with a coil (not shown), which MR images can be displayed on a display unit 709. The MR system can be controlled by an operator with an operating unit 710. The other typical components of an MR system have been omitted for clarity.

The method steps described in the following in connection with FIG. 1 can, for example, be implemented with the aid of the MR image computer 708 or a processing unit integrated into the display unit 709.

Figure 1:
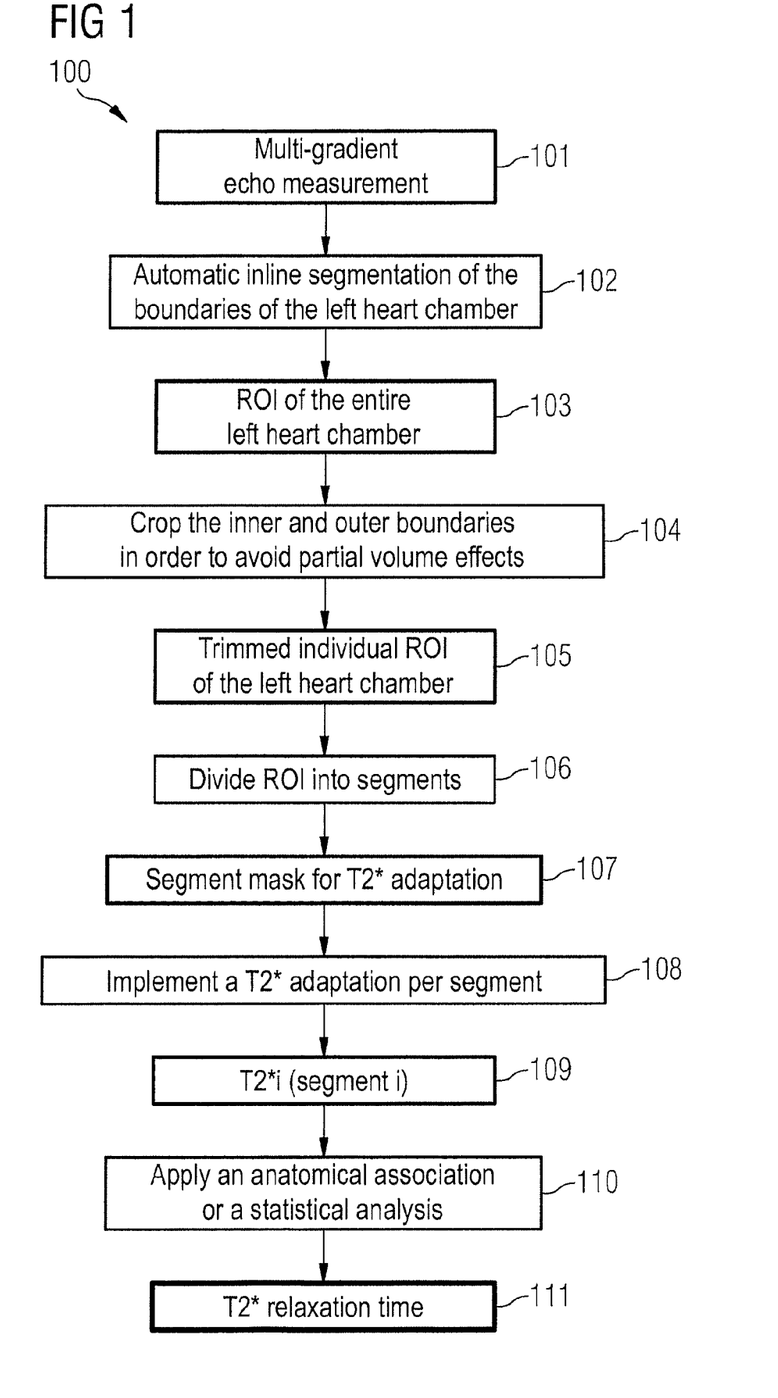
FIG. 1 is a flowchart of a method to determine a T2* relaxation time in the heart muscle in a magnetic resonance examination according to an embodiment of the present invention.

FIG. 1 is a flowchart 100 of an embodiment of a method to determine a T2* relaxation time in the heart muscle in a magnetic resonance examination. Although it is primarily embodiments of the present invention that are described in the following with regard to a determination of a T2* relaxation time, the method of the present invention is likewise applicable to a determination of an arbitrarily different MR relaxation time in a magnetic resonance examination of the heart muscle, for example in a determination of a T1 relaxation time or a T2 relaxation time.

Figure 2:
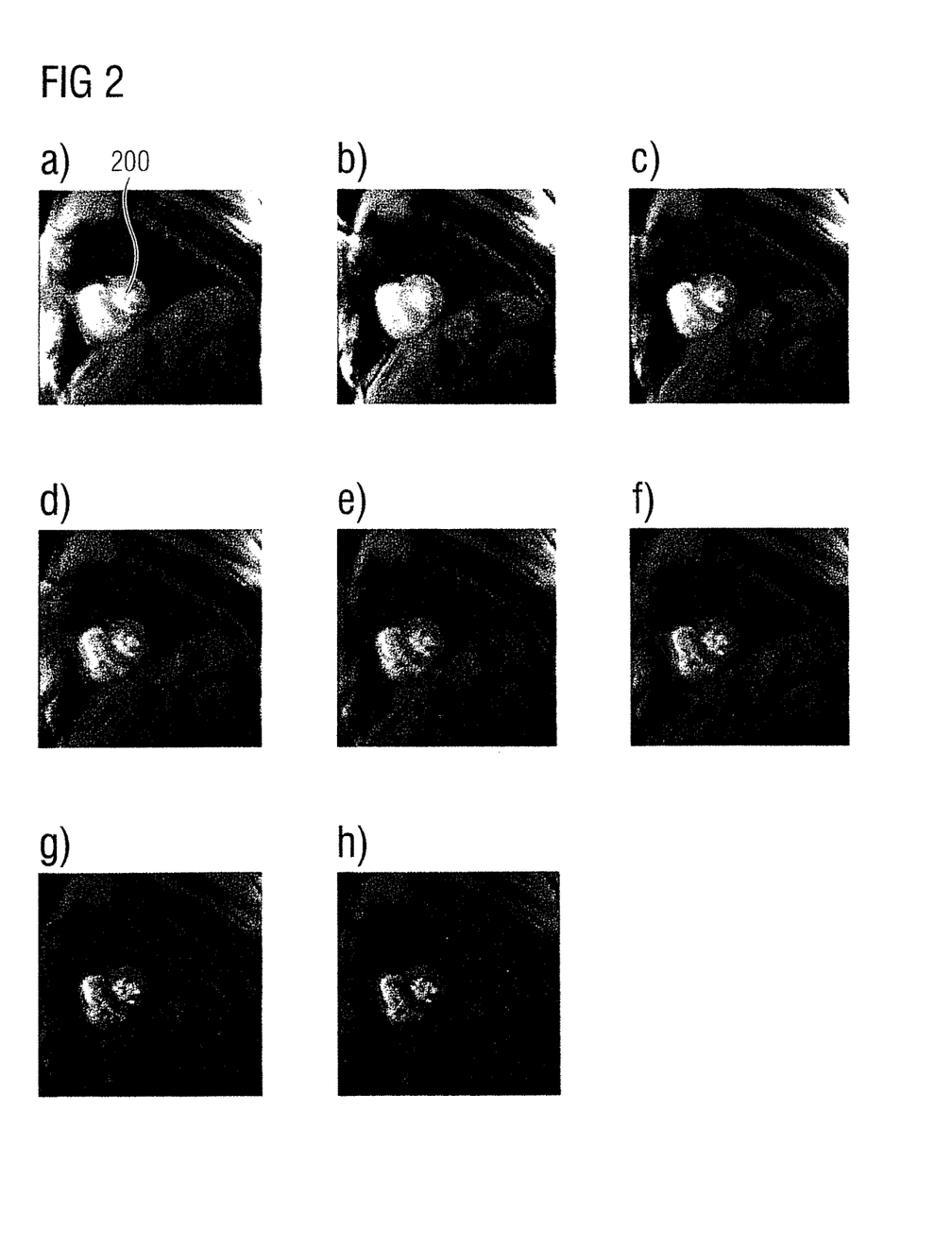
FIG. 2 shows images of a multi-gradient echo measurement with different echo times.

In a first Step 101, a multi-gradient echo measurement with suitably selected echo times is implemented. FIG. 2a)-2h) show eight individual images of the multi-gradient echo measurement with different echo times TE in a range from 2.6 ms to 18.2 ms. Each of the individual images shows a slice image through the heart muscle (myocardium). The individual images differ due to the different echo times in their contrast. The left heart chamber 200 (left ventricle) is clearly visible in each of the individual images.

An automatic inline segmentation of the left heart chamber 200 is implemented in the next Step 102 of the method shown in FIG. 1. The result of this segmentation (which can be implemented with typical inline segmentation methods) is shown for an individual image in FIG. 3. The inline segmentation delivers an outer edge 300 (what is known as an epicardial boundary line) and an inner edge 301 (what is known as a subendocardial boundary line) of the muscle tissue of the left heart chamber 200. This annular region which is located between the boundary lines 300 and 301 is considered in detail to determine the T2* relaxation time and therefore will be designated in the following as the region of interest ROI (Step 103 in FIG. 1).

Figure 3:
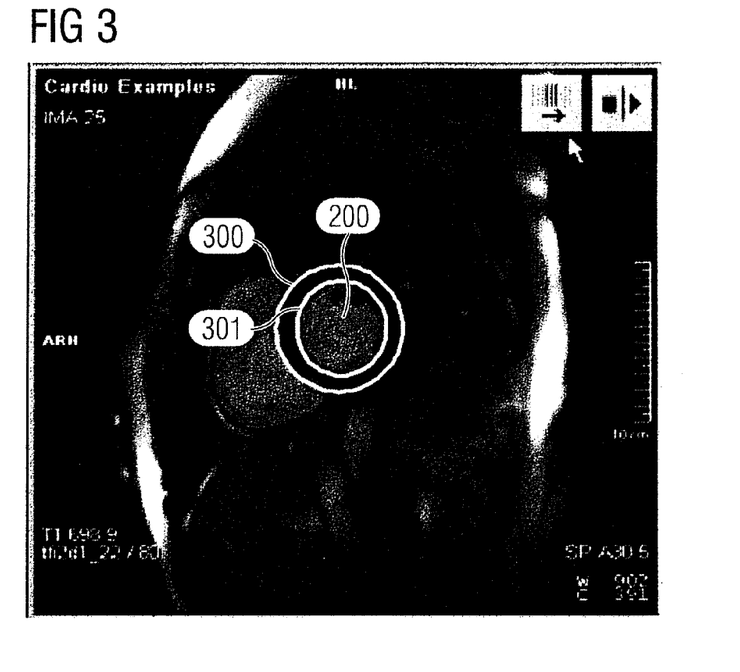
FIG. 3 shows a magnetic resonance image of a heart muscle with an annular slice image region of the left heart chamber determined therein.
Figure 4:
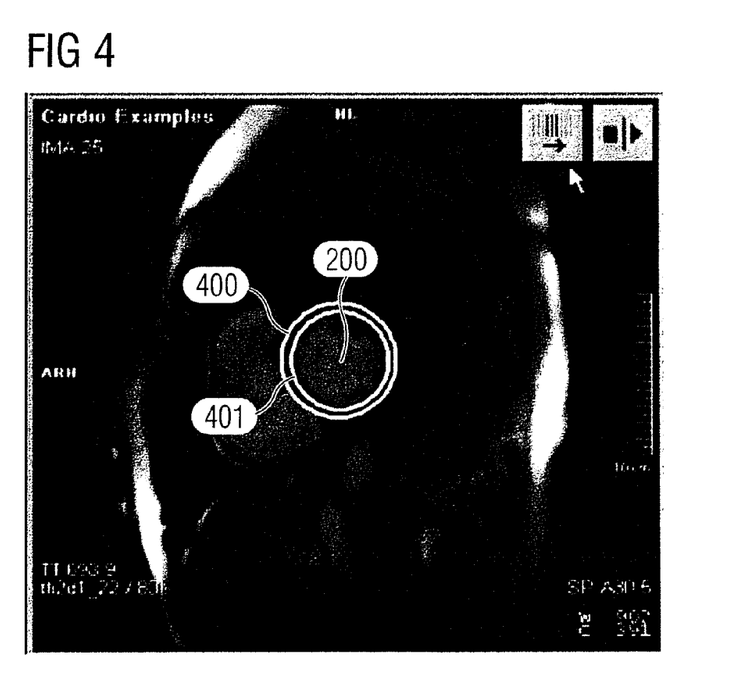
FIG. 4 shows the magnetic resonance image of FIG. 3 with a reduced slice image region of the left heart chamber.

In a further Step 104 of the method 100, the ROI is reduced in order to avoid partial volume effects. For this the periphery of the outer boundary line 300 is reduced in the radial direction and the periphery of the inner boundary line 301 is enlarged in the radial direction. The result of the trimmed ROI of the left heart chamber is shown in FIG. 4 (Step 105). The reduced outer boundary line 300 of FIG. 3 is represented by the boundary line 400 in FIG. 4. The enlarged boundary line 301 of FIG. 3 is represented by the boundary line 401 in FIG. 4.

Figure 5:
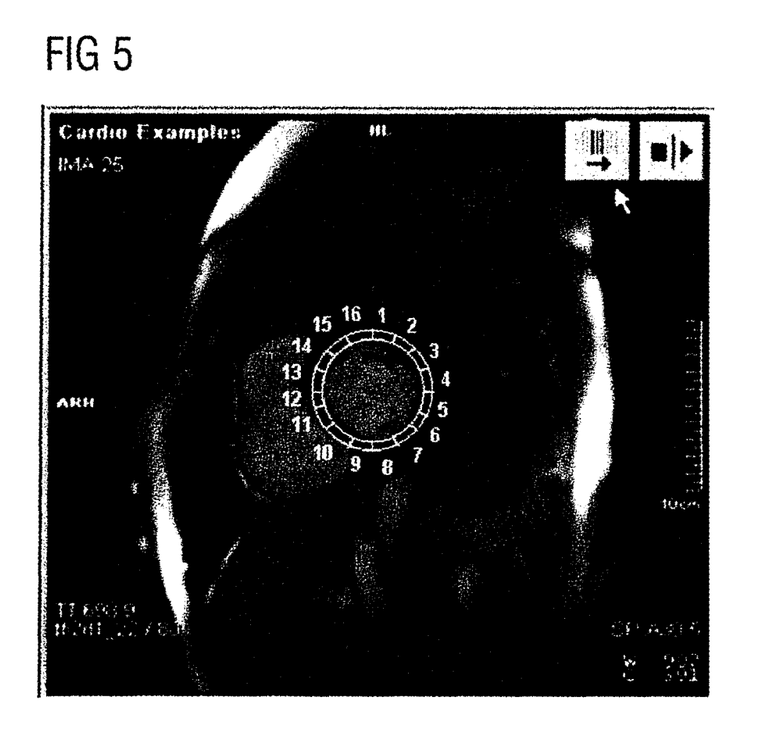
FIG. 5 shows the magnetic resonance image of FIG. 4 with a slice image region of the left heart chamber subdivided into sub-regions.

In a further Step 106 of the method 100, the ROI bounded by the boundary lines 400 and 401 is subdivided into sub-regions or segments. In the present embodiment, the ROI of FIG. 4 is divided into 16 sub-regions 1-16, as is shown in FIG. 5 (Step 107 in FIG. 1).

In Step 108 of the method 100, a T2* adaptation is implemented for each segment 1-16 or, respectively, for each sub-region 1-16. For this the signal intensities of every sub-region 1-16 are respectively approximated as a function of the echo time with an exponential fit, from which results the T2* relaxation time for this sub-region.

Figure 6:
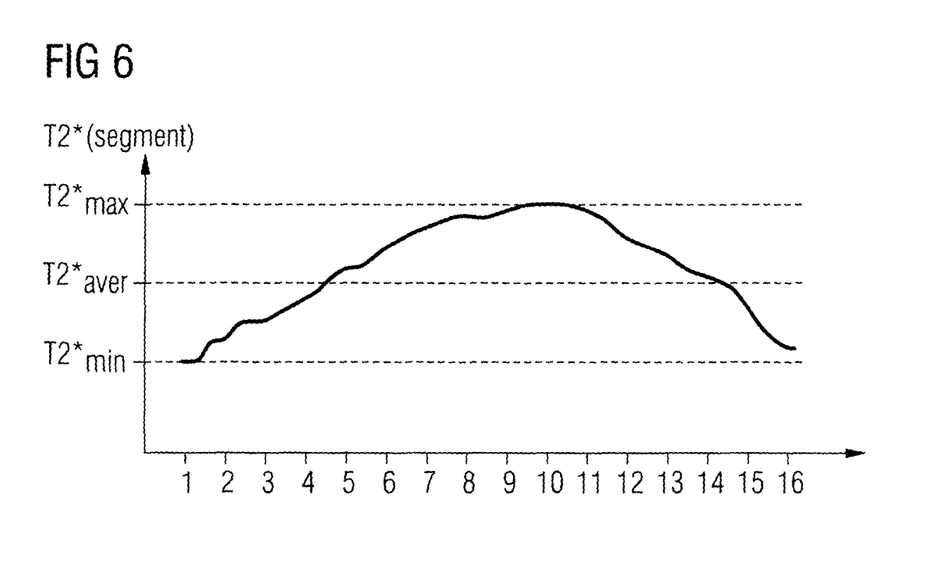
FIG. 6 is a diagram of the T2* relaxation times of the multiple sub-regions of FIG. 5

In Step 109 of the method 100, the T2* relaxation times determined for each sub-region 1-16 or each segment 1-16 (as shown in FIG. 6) are plotted as a function over the sub-regions 1-16.

In Step 110 of the method 100, a statistical analysis is applied to the T2* relaxation times shown in FIG. 6 in order to determine a characteristic T2* relaxation time in the heart muscle (Step 111). The statistical analysis can be implemented, for example, such that an average of the established T2* relaxation times is determined and this average is used as a characteristic T2* relaxation time. Alternatively a subset of the individual T2* relaxation times can be formed which, for example, comprises only the longest T2* relaxation times. The size of the subset can be selected, for example, such that the subset is approximately half of the determined T2* relaxation times of the sub-regions. An average of the T2* relaxation times of the determined subset is then used as a characteristic T2* relaxation time in the heart muscle.

Alternatively, through an anatomical association a user can determine the relevant T2* relaxation values from the T2* curve of sub-regions 1-16 shown in FIG. 6, and a characteristic T2* relaxation value can be determined in this manner.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to determine a magnetic resonance (MR) relaxation time in a heart muscle in a magnetic resonance examination, comprising the steps of:

using a computer to operate an MR data acquisition apparatus in order to acquire MR data from an examination subject, while the examination subject is situated in the MR data acquisition apparatus, from heart muscle tissue of the left heart chamber of the examination subject;

in said computer, reconstructing an image from said MR data, said image being comprised of pixels that each exhibit a signal intensity, said image depicting anatomy of the heart muscle tissue at the left heart chamber of the examination subject;

in said computer, (a) implementing an automatic image segmentation of said anatomy in said image to determine an annular slice image region, comprised of pixels of said image of the heart muscle tissue of the left heart chamber so that said annular slice region has a width in a radial direction that is reduced by an inner periphery of the annular slice image region being increased by a predetermined value and an outer periphery of the annular slice image region being reduced by a predetermined value;

in said computer, (b) automatically dividing said annular slice image region of said image of the heart muscle tissue of the left heart chamber into a plurality of sub-regions of said annular slice image region of said image, each sub-region comprising a sub-plurality of said plurality of said pixels of said annular slice image region of the heart muscle tissue of the left heart chamber, each of said pixels in each sub-region exhibiting said signal intensity;

for each of said sub-regions, (c) automatically determining, in said computer, an MR relaxation time of the heart muscle tissue depicted in the respective sub-region from the respective signal intensities of the respective pixels thereof, thereby obtaining a plurality of MR relaxation times; and in said computer, (d) automatically quantifying a characteristic MR relaxation time, of all the heart muscle, by statistical analysis of said plurality of MR relaxation times of the heart muscle tissue depicted in the respective sub-regions, and making a representation of the quantified characteristic MR relaxation time of all the heart muscle tissue available in electronic form at an output of the computer.

2. A method as claimed in claim 1 comprising employing, as said MR relaxation times of the respective sub-regions and said MR relaxation time of the heart muscle, an MR relaxation time selected from the group consisting of a T2* relaxation time, a T1 relaxation time and a T2 relaxation time.

3. A method as claimed in claim 1 wherein the step of providing a computerized processor with an image comprises providing said computerized processor with comprising using said computer to operate said MR data acquisition apparatus in order to acquire multiple images respectively at different times, selected from the group consisting of different echo times and different inversion times, and comprising performing (a), (b), (c) and (d) for each of said multiple images.

4. A method as claimed in claim 1 comprising using said computer to operate said MR data acquisition apparatus in order to acquire multiple images respectively acquired at different echo times in a range between 2 ms and 20 ms, and comprising performing (a), (b), (c) and (d) for each of said multiple images.

5. A method as claimed in claim 1 wherein said predetermined value in a range between 1 mm and 10 mm.

6. A method as claimed in claim 1 wherein said predetermined value in a range between 5% and 30% of said width.

7. A method as claimed in claim 1 comprising, in (b), subdividing the annular slice image region of the heart muscle of the left heart chamber into a plurality of sub-regions that respectively represent different annular segments of the annular slice image region of the heart muscle of the left heart chamber.

8. A method as claimed in claim 1 wherein said range of MR relaxation times have respective values in a range between a smallest value and a largest value, and comprising, in (c), implementing said statistical analysis to determine said MR relaxation time of the heart muscle from an average value of a predetermined number, of said plurality of MR relaxation times of the respective sub-regions, and employing as said predetermined number a number of said plurality of MR relaxation times comprising an upper half of said range that includes said largest value.

9. A magnetic resonance (MR) system to determine an MR relaxation time in the heart muscle of an examination subject in a magnetic resonance examination, comprising:
  an MR data acquisition apparatus
  a computer configured to operate said MR data acquisition apparatus, while an examination subject is situated therein, in order to acquire MR data from the examination subject from heart muscle tissue of the left heart chamber of the examination subject, and to reconstruct an image, comprised of pixels that each exhibit a signal intensity, from said MR data, said image depicting anatomy of said portion of the heart muscle tissue of the left heart chamber of the examination subject; and
  said computer being configured to automatically implement an image segmentation of said anatomy in said image to determine annular slice image region, comprised of pixels in said image, so that said annular slice region has a width in a radial direction that is reduced by an inner periphery of the annular slice image region being increased by a predetermined value and an outer periphery of the annular slice image region being reduced by a predetermined value of the heart muscle tissue of the left heart chamber in said image, and to automatically divide said annular slice image region into a plurality of sub-regions within said annular slice image region, each sub-region comprising a sub-plurality of said plurality of said pixels of said annular slice image region of the heart muscle tissue of the left heart chamber, each of said pixels in each of said sub-regions exhibiting said signal intensity and to automatically determine, for each of said sub-regions of said image, an MR relaxation time of the heart muscle tissue depicted in the respective sub-region from the respective signal intensified of the respective pixels thereof, thereby obtaining a plurality of MR relaxation times, and to automatically quantify a characteristic MR relaxation time of all the heart muscle by statistically analyzing said plurality of MR relaxation times of the respective sub-regions, and said computer being configured to make a representation of the quantified characteristic MR relaxation time of all the heart muscle available in electronic form at an output of the computer.

10. A non-transitory computer-readable storage medium encoded with programming instructions, said storage medium being loadable into a computerized control and evaluation system of a magnetic resonance (MR) system that also comprises an MR data acquisition apparatus, said programming instructions causing said computerized control and evaluation unit to:
  operate said MR data acquisition apparatus in order to acquire magnetic resonance data from heart muscle tissue of the left heart chamber of an examination subject in the MR data acquisition apparatus, and reconstruct an image, comprised of pixels each exhibiting a signal intensity, from said MR data, said image depicting anatomy of said heart muscle tissue of the left heart chamber of the examination subject;
  automatically implement an image segmentation of said anatomy in in said image to determine an annular slice image region, comprised of pixels of said image, of the heart muscle of the left heart chamber in said image so that said annular slice region has a width in a radial direction that is reduced by an inner periphery of the annular slice image region being increased b a predetermined value and an outer periphery of the annular slice image region being reduced by a predetermined value;
  automatically divide said annular slice image region into a plurality of sub-regions within the annular slice image region, each sub-region comprising a sub-plurality of said plurality of said pixels of the annular slice image of the heart muscle of the left heart chamber each of said pixels in each of said sub-regions exhibiting said signal intensity;
  for each of said plurality of sub-regions in said image, automatically determine an MR relaxation time of the heart muscle tissue depicted in the respective sub-region from the respective signal intensified of the respective pixels thereof, thereby obtaining a plurality of MR relaxation times; and
  automatically quantify a characteristic MR relaxation time of all the heart muscle tissue by implementing a statistical analysis of said plurality of MR relaxation times of the respective sub-regions, and make a representation of the quantified characteristic MR relaxation time of all the heart muscle tissue available in electronic form at an output of the control and evaluation system.

* * * * *